US012622607B2

(12) United States Patent
Sur et al.

(10) Patent No.: US 12,622,607 B2
(45) Date of Patent: May 12, 2026

(54) HUMAN SLEEP POSTURE EXTRACTION FROM MILLIMETER-WAVE WIRELESS SYSTEMS

(71) Applicant: UNIVERSITY OF SOUTH CAROLINA, Columbia, SC (US)

(72) Inventors: Sanjib Sur, Cayce (IN); Aakriti Adhikari, Columbia (IN)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 16 days.

(21) Appl. No.: 18/436,186

(22) Filed: Feb. 8, 2024

(65) Prior Publication Data

US 2024/0350037 A1 Oct. 24, 2024

Related U.S. Application Data

(60) Provisional application No. 63/497,218, filed on Apr. 20, 2023.

(51) Int. Cl.
| | |
|---|---|
| *A61B 5/11* | (2006.01) |
| *A61B 5/00* | (2006.01) |
| *A61B 5/05* | (2021.01) |

(52) U.S. Cl.
CPC .............. *A61B 5/1126* (2013.01); *A61B 5/05* (2013.01); *A61B 5/1114* (2013.01);
(Continued)

(58) Field of Classification Search
CPC ... A61B 5/35; A61B 5/7267; A61B 2090/364; A61B 2034/104; A61B 5/4806;
(Continued)

(56) References Cited

U.S. PATENT DOCUMENTS

| | | | |
|---|---|---|---|
| 2017/0172308 A1* | 6/2017 | North | A61B 5/02 |
| 2021/0100451 A1* | 4/2021 | Cao | A61B 5/1116 |

(Continued)

OTHER PUBLICATIONS

Maytus [SleepPoseNet: Multi-View Learning for Sleep Postural Transition Recognition Using UWB, IEEE Journal of Biomedical and Health Informatics, vol. 25, No. 4, Apr. 2021] (Year: 2021).*

(Continued)

*Primary Examiner* — Oommen Jacob
(74) *Attorney, Agent, or Firm* — DORITY & MANNING, P.A.

(57) ABSTRACT

Methodology and corresponding apparatus pertain to human sleep posture monitoring, using a wireless signal-based monitoring system leveraging millimeter-wave technology. A software-only human sleep posture monitoring solution based on millimeter-wave (mmWave) wireless-based solutions enables fine-grained posture monitoring under no light without being privacy-invasive. In zero visibility, body joint information and changes can be extracted directly from mmWave imaging using improved capabilities for extracting human sleep posture data from millimeter-wave wireless systems. A single-person sleep posture monitoring system leverages signal processing and deep learning models to enable fine-grained monitoring continuously and non-intrusively with commodity (i.e., generally available) mmWave devices. The system directly predicts joint locations from reflected mmWave signals by learning the hidden association between them from thousands of data samples. Learning is accomplished through a customized Deep Convolutional Neural Network (DCNN), that predicts the 3D locations of several key body joints from the reflected signals captured by multiple mmWave antennas.

14 Claims, 5 Drawing Sheets

(52) U.S. Cl.
CPC .......... *A61B 5/1116* (2013.01); *A61B 5/4806* (2013.01); *A61B 5/7203* (2013.01); *A61B 5/7267* (2013.01); *A61B 5/7275* (2013.01)

(58) Field of Classification Search
CPC ... A61B 5/4803; A61B 5/4821; A61B 5/4815; G06N 7/01; G06N 3/088; G06N 20/10
See application file for complete search history.

(56) References Cited

U.S. PATENT DOCUMENTS

| | | | | |
|---|---|---|---|---|
| 2021/0100480 | A1* | 4/2021 | Kang | G06N 3/08 |
| 2021/0197834 | A1* | 7/2021 | Shaker | G06V 40/25 |
| 2024/0053464 | A1* | 2/2024 | Dahnoun | G01S 13/886 |
| 2024/0350037 | A1* | 10/2024 | Sur | A61B 5/1116 |

OTHER PUBLICATIONS

Sizhe [MARS: mmWave-based Assistive Rehabilitation System for Smart Healthcare, ACM Trans. Embedd. Comput. Syst., vol. 1, No. 1, Article 1. Publication date: Jan. 2021] (Year: 2021).*

Albawi et al. Understanding of a convolutional neural network, in 2017 International Conference on Engineering and Technology (ICET), 2017.

Amazon, "Tactilus Mattress Pressure Mapping Sensor System Tactile Force Bed Software Body," 2022. [Online . Available: https://www.amazon.com/TACTILUS-Mattress-Pressure-Mapping-Software/.

AMW Porter "The Prediction of Physique from the Skeleton." International Journal of Osteoarchaeol, vol. 9, 1999.

Blazevic et al. "Towards Reversible De-Identification in Video Sequences Using 3D Avatars and Steganography," 2015 Proceedings of the Croatian Computer Vision Workshop.

Chen et al."Anatomy-aware 3D Human Pose Estimation with Bone-based Pose Decomposition," 2020. IEEE Transactions on Circuits and Systems for Video Technology.

Desouzart et al. "Effects of Sleeping Position on Back Pain in Physically Active Seniors: A Controlled Pilot Study," Work, vol. 53, No. 2, 2013.

Johns Hopkins, "Choosing the Best Sleep Position," 2022. (Available online https://www.hopkinsmedicine.org/health/wellness-and-prevention/choosing-the-best-sleep-position).

Joosten et al. "Supine Position Related Obstructive Sleep Apnea in Adults: Pathogenesis and Treatment," Sleep Medicine Reviews, vol. 18, No. 1, 2014.

Kwon et al. "Recent Advances in Wearable Sensors and Portable Electronics for Sleep Monitoring," iScience, vol. 24, No. 5, 2021.

Lee et al. "Sleep Monitoring System Using Kinect Sensor," International Journal of Distributed Sensor Networks, 2015.

Lee et al. "The Effect of Body Posture on Brain Glymphatic Transport," Journal of Neuroscience, vol. 35, No. 31, 2015.

Liu et al. "A Vision-Based System for In-Bed Posture Tracking," in 2017 IEEE International Conference on Computer Vision Workshops (ICCVW), 2017.

Liu et al. "Sleep Posture Analysis Using a Dense Pressure Sensitive Bedsheet," Pervasive and Mobile Computing, vol. 10, 2014.

Matricciani et al. "Rethinking the Sleep-Health Link," Sleep Health, vol. 4, No. 4, 2018.

Pin et al. "A Review of the Effects of Sleep Position, Play Position, and Equipment Use on Motor Development in Infants," Developmental Medicine and Child Neurology, vol. 49, No. 11, 2007.

Rebecca Flood "Dream Team People Are Arguing About What is the Best Position to Sleep in but Which One Are You?" The Sun 2020. (Available online https://www.the-sun.com/lifestyle/291019/people-are-arguing-about-what-is-the-best-position-to-sleep-in-but-which-one-are-you/).

Simonyan et al. "Very Deep Convolutional Networks for Large-Scale Image Recognition," 2015 ICLR.

Stefani et al. "Sleep in Parkinson's disease," Neuropsychopharmacology, vol. 45, No. 1, 2020.

Suni et al. "Best Sleeping Positions," 2022. Sleep Foundation (Available online https://www.sleepfoundation.org/sleeping-positions).

World Population Review, "Average Height by State 2022," 2022. (Available Online https://worldpopulationreview.com/state-rankings/average-height-by-state).

Zhang et al. "mmEye: Super-Resolution Millimeter Wave Imaging," IEEE Internet of Things Journal, vol. 8, No. 8, 2021.

* cited by examiner

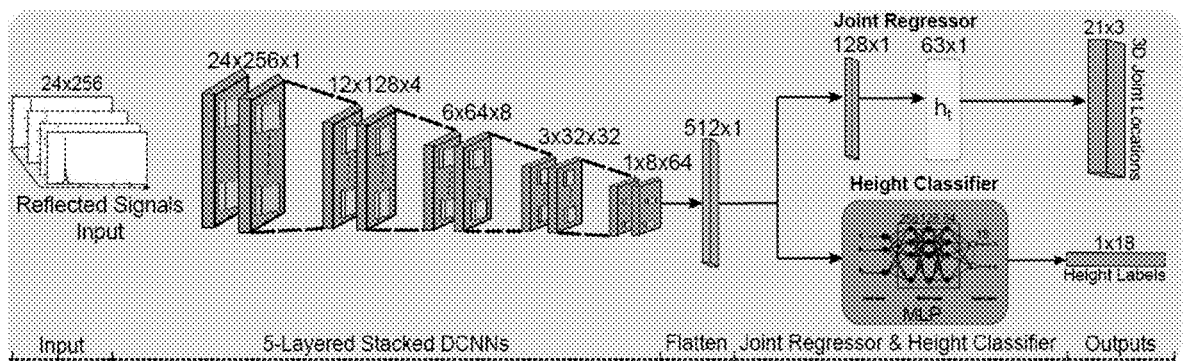
FIG. 2(a)
TABLE 1
| Stack | C1 S1,S2 | C2 S1,S2 | C3 S1,S2 | C4 S1,S2 | C5 S1,S2 | FL | FC1 | FC2 | Output |
|---|---|---|---|---|---|---|---|---|---|
| Filter # | 4 | 8 | 16 | 32 | 64 | 512 | 128 | 63 | 21x3 |
| Filter Size | 6x6 | 6x6 | 6x6 | 6x6 | 6x6 | | | | |
| Dilation | 2x2, 1x1 | 2x2, 1x1 | 2x2, 1x1 | 2x2, 1x1 | 2x2, 1x1 | | | | |
| Act. Fcn. | LReLU | LReLU | LReLU | LReLU | LReLU | | LReLU | Linear | |
FIG. 2(b)
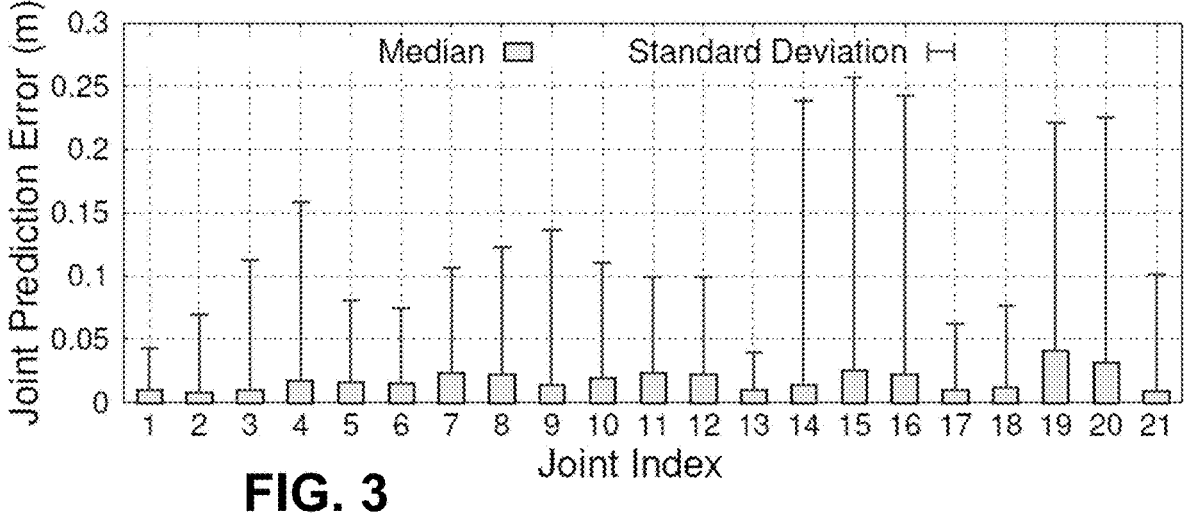
FIG. 3

HUMAN SLEEP POSTURE EXTRACTION FROM MILLIMETER-WAVE WIRELESS SYSTEMS

PRIORITY CLAIM

The present application claims the benefit of priority of U.S. Provisional Patent Application No. 63/497,218, titled Human Sleep Posture Extraction From Millimeter-Wave Wireless Systems, filed Apr. 20, 2023, and which is fully incorporated herein by reference for all purposes.

STATEMENT REGARDING SPONSORED RESEARCH OR DEVELOPMENT

This invention was made with government support under Grant Number 2144505, awarded by the NSF. The government has certain rights in the invention.

BACKGROUND OF THE PRESENTLY DISCLOSED SUBJECT MATTER

1. Importance, Challenges, and Prior Art

Humans spend approximately one-third of their life sleeping. High-quality sleep is of vital importance for the short term proper functioning of the human body and for long-term good health [1]. A key metric to monitoring sleep is the spatial and temporal understanding of sleep postures through the night, as the postures directly influence sleep behavior and critical parameters [2]. Each of us sleeps in one of the broad categories of posture, such as supine, lateral, fetal, etc., and exhibits wide variations of them throughout the night [3]. The effect of different sleep postures has been studied widely to identify their relationship to different health conditions [4-6].

Specific sleep postures could be fatal depending on the pre-existing medical conditions. For example, supine posture is linked with exacerbating obstructive sleep apnea by creating unfavorable airway geometry, causing a reduction in lung volume and limiting the movement of airway dilator muscles, which could be life-threatening [7]. Infrequent turns due to impairment in control of the motor activity of Parkinson's patients lead to parasomnia and restless leg syndrome [8]. Infrequent changes in sleep posture are also the primary cause of pressure ulcers (i.e., bedsores) in post-surgical and elderly patients.

Additionally, physicians recommend different sleep postures for different medical conditions: It is recommended to sleep on side posture to reduce snoring, or left side to prevent heartburn, or supine posture to lower back or shoulder pain, or fetal posture during pregnancy, or some specific posture variations during post-surgery recovery [9; 10].

These examples highlight the importance of a sleep posture monitoring system that can provide real spatio-temporal observations, which could help with corrections and prevent fatal accidents.

Existing at-home approaches for sleep posture monitoring that use wearables, pressure mattresses, or vision cameras are either cumbersome, costlier, or highly privacy-invasive [11-14].

Further, their performance is hindered by dark bedroom conditions and occlusion. Millimeter-wave (mmWave) wireless-based solutions can overcome these challenges by enabling fine-grained posture monitoring under no light without being privacy-invasive. MmWave signals can penetrate certain obstacles, work under zero visibility, and have higher-resolution than Wi-Fi. So, mmWave imaging can facilitate "seeing" the body posture under dark conditions and under the blanket. Besides, mmWave transceivers are poised to soon become ubiquitous in all 5G-and-beyond devices, such as access points, enabling the opportunity for bringing privacy non-invasive sleep posture monitoring system to the masses at-home.

However, there exist two fundamental challenges in mmWave imaging. First, mmWave signals could be absorbed by many body parts or specularly reflect from them in different directions away from the device, causing most signals to never reach back to the receiver. So, the output human shape could have a lot of missing parts from which it is difficult to infer joint locations.

Second, mmWave devices have extremely low-resolution compared to vision-based systems; so, many high-frequency components, such as the contour and limbs, will be eliminated from the generated images [15]. Moreover, the reflected signals carry additional information about the bed and surrounding objects close to the body, making it harder to separate the human shape.

So, it is challenging to extract body joint information and changes directly from traditional mmWave imaging during sleep.

SUMMARY OF THE PRESENTLY DISCLOSED SUBJECT MATTER

The presently disclosed systems and corresponding and/or associated methodologies generally relate to improved mmWave imaging technology, and more particularly to improved capabilities for extracting human sleep posture data from millimeter-wave wireless systems.

Presently disclosed subject matter (also in some instances presently referenced as "MiSleep") is for some embodiments a wireless signal based sleep posture monitoring system. MiSleep leverages the built-in millimeter-wave technology on ubiquitous 5G wireless devices and provides a software-only sleep posture monitoring solution, so it does not require any extra hardware as do existing pressure mattress technologies.

To overcome above-referenced challenges for some settings, the presently disclosed MiSleep technology makes possible a single-person sleep posture monitoring system that leverages signal processing and deep learning models to enable fine-grained monitoring continuously and non-intrusively with commodity (i.e., generally available) mmWave devices.

It is to be understood that the presently disclosed subject matter equally relates to associated and/or corresponding methodologies and operative devices or technologies. One exemplary such method relates to methodology for identifying sleep posture of a human subject, comprising transmitting millimeter-wave (mmWave) wireless signals configured for interacting with a human subject; receiving millimeter-wave (mmWave) wireless signals reflecting from the human subject; predicting joint locations of the human subject based on the received signal reflections; and based on predicted joint locations of the human subject, classifying the sleep posture of the human subject into one of a plurality of diverse sleep postures during the rest state of the human subject.

Another exemplary such method relates to method for automatically classifying sleep postures of a human subject from millimeter-wave (mmWave) wireless signals reflecting from the human subject, comprising training a Deep Convolutional Neural Network (DCNN) learning model, based on inputs of ground truth sleep postures of a plurality of human subjects and corresponding generated input-output pairs of mmWave reflected signals from the plurality of human subjects, to learn the association between millimeter-wave (mmWave) wireless signals reflected from a human subject and joint locations of a human subject; and operating the trained DCNN learning model to process further input data thereto, to determine and output identification of diverse sleep postures during the rest state of the human subject.

Other example aspects of the present disclosure are directed to systems, apparatus, tangible, non-transitory computer-readable media, user interfaces, memory devices, and electronic devices for improved mmWave imaging technology. To implement methodology and technology herewith, one or more processors may be provided, programmed to perform the steps and functions as called for by the presently disclosed subject matter, as will be understood by those of ordinary skill in the art.

Another exemplary embodiment of presently disclosed subject matter relates to one or more tangible, non-transitory computer-readable media that collectively store instructions that, when executed, cause a computing device including one or more processors to perform operations, the operations comprising automatically identifying diverse sleep postures during the rest state of a human subject from millimeter-wave (mmWave) wireless signals reflecting from the human subject, by training a Deep Convolutional Neural Network (DCNN) learning model, based on inputs of ground truth sleep postures of a plurality of human subjects and corresponding generated input-output pairs of mmWave reflected signals from the plurality of human subjects, to learn the association between millimeter-wave (mmWave) wireless signals reflected from a human subject and joint locations of a human subject; and operating the trained DCNN learning model to process further input data thereto, to determine and output identification of diverse sleep postures during the rest state of the human subject.

Additional objects and advantages of the presently disclosed subject matter are set forth in, or will be apparent to, those of ordinary skill in the art from the detailed description herein. Also, it should be further appreciated that modifications and variations to the specifically illustrated, referred and discussed features, elements, and steps hereof may be practiced in various embodiments, uses, and practices of the presently disclosed subject matter without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the presently disclosed subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the presently disclosed subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification, and will appreciate that the presently disclosed subject matter applies equally to corresponding methodologies as associated with practice of any of the present exemplary devices, and vice versa.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 2(a) diagrammatically illustrates an exemplary embodiment of a presently disclosed Rest Network architecture, with two major components: Joint Regressor and Height Classifier;

FIG. 2(b) illustrates a table (Table I) of specifications for an exemplary DCNN, specifically including exemplary Joint Regressor network parameters for a presently disclosed embodiment of MiSleep;

FIG. 3 graphically illustrates median and standard deviation data for a presently disclosed exemplary system (MiSleep's) prediction errors for 21 joints across 5 poses for 3 volunteers;

Figure 1A:
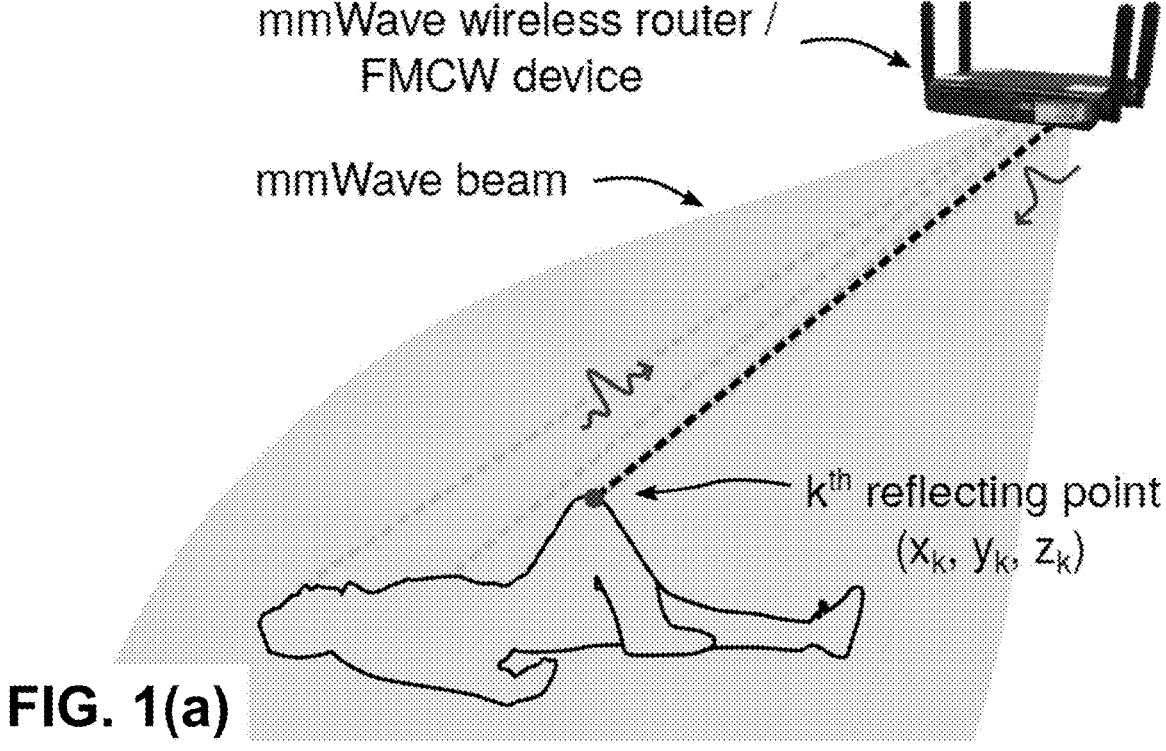
FIGS. 1(a) and 1(b) show examples of mmWave reflections involving a sleeping human, with FIG. 1(a) in particular diagrammatically illustrates an exemplary embodiment of a mmWave device capturing reflected signals from a human target, while FIG. 1(b) graphically illustrates comparative examples of reflected signals from two respective sleep postures of human targets.

Repeat use of reference characters in the present specification and drawings is intended to represent the same or analogous features, elements, or steps of the presently disclosed subject matter.

DETAILED DESCRIPTION OF THE PRESENTLY DISCLOSED SUBJECT MATTER

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

2. Disclosed Approach

In general, the present disclosure is directed to presently disclosed systems and corresponding and/or associated methodologies generally relate to improved mmWave imaging technology, and more particularly to improved capabilities for extracting human sleep posture data from millimeter-wave wireless systems. Per some presently disclosed embodiments, wireless signal based sleep posture monitoring technology leverages built-in millimeter-wave technology on commonly available 5G wireless devices and provides a software-only sleep posture monitoring solution. In such situations, no extra hardware such as existing pressure mattress technologies, is required.

Figure 1B:
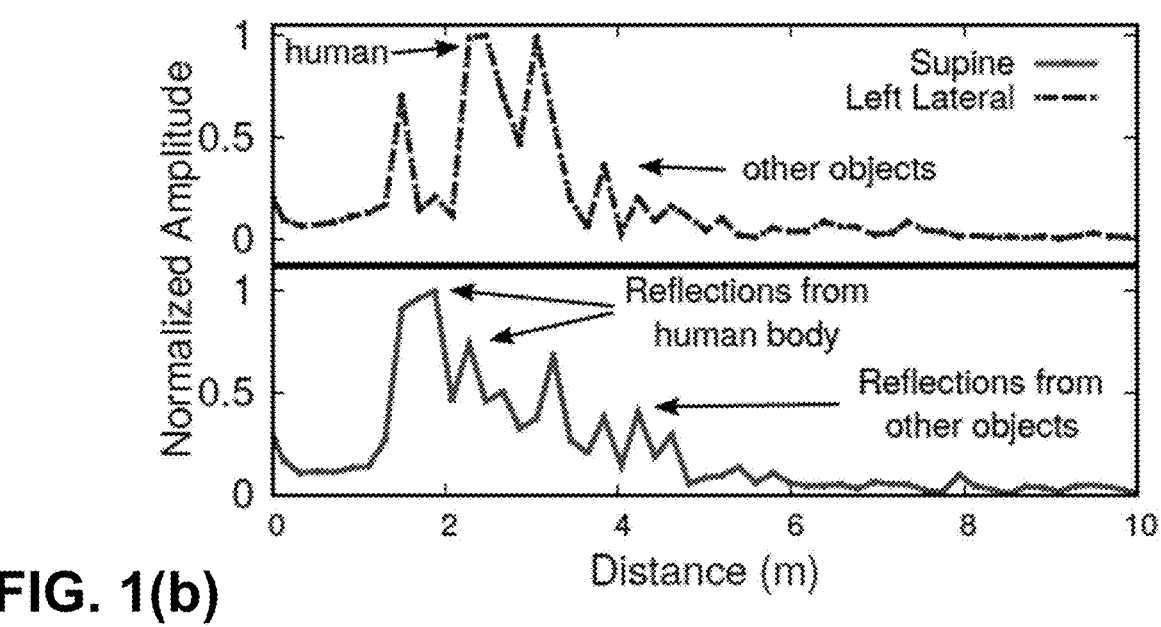

FIGS. 1(a) and 1(b) show examples of mmWave reflections involving a sleeping human. In particular, FIG. 1(a) diagrammatically illustrates an exemplary embodiment of a mmWave device capturing reflected signals from a human target, while FIG. 1(b) graphically illustrates comparative examples of reflected signals from two respective sleep postures of human targets. For example, FIG. 1(a) represents exemplary use of a mmWave wireless router which may be associated with or implemented as a Frequency Modulated Continuous Wave (FMCW) device. An FMCW device may be a form of radar where the frequency of the transmitted signal is continuously varied at a known rate over a defined time period, with the reflected frequency signal as received by the radar then compared.

Instead of generating a mmWave image from traditional algorithms and then predicting the body joint locations, the presently disclosed subject matter (also referred herein for some embodiments thereof as "MiSleep") directly predicts the joint locations from the reflected mmWave signals by learning the hidden association between them from thousands of data samples. To learn such an association, MiSleep employs a customized Deep Convolutional Neural Network (DCNN), that predicts the 3D locations of several key body joints from the reflected signals captured by multiple mmWave antennas. Furthermore, to generalize the model for diverse populations, MiSleep models a height classifier and uses the error in its prediction to finetune the model. We implement our system on off-the-shelf components and demonstrate performance, qualitatively and quantitatively.

2.1. Design of a Presently Disclosed Exemplary Embodiment

The core purpose of the herein-referenced "Rest Network" is to predict the 3D location of body joints from the mmWave signal reflections and capture diverse sleep postures during the rest state. The Rest Network is designed using a customized Deep Convolutional Neural Network (DCNN) called Joint Regressor to map the relevant higher-dimensional features in input to output.

The Joint Regressor is trained with two human-anatomy specific features. First, 3D location of body joints of an individual is correlated with her height [16]; so, MiSleep could constrain and finetune the prediction for joint locations by predicting the height and comparing the difference with the known height of the user. Then, the model can output better 3D joint locations by backpropagating the height prediction error, and the network can be generalizable for many users.

Second, most of the human body joints are spatially connected to each other in a parent-child, tree-like hierarchy [17], and 3D pose of one joint is usually constrained by its parent's pose. So, the 3D location output of a child should be conditioned on its parent joint to ensure the distance between the parent and child is always fixed, across all postures.

FIG. 2(a) diagrammatically illustrates an exemplary embodiment of a presently disclosed Rest Network architecture, with two major components: Joint Regressor and Height Classifier, which are further discussed herein. FIG. 2(b) illustrates a table (Table I) of specifications for an exemplary DCNN, specifically including exemplary Joint Regressor network parameters for a presently disclosed embodiment of MiSleep, including Cj: $j^{th}$ Convolutional layer; Si: $i^{th}$ Stack in $j^{th}$ Convolutional layer; FL: Flatten layer; FC: Fully Connected layer; Act. Fcn.: Activation Function. LReLU: Leaky ReLU.

Joint Regressor: The objective of the Joint Regressor is to capture the hidden relationship between mmWave reflections and 3D joint locations to infer the complete posture by using a customized DCNN as the Feature Extractor. A DCNN maps relevant features in input to output by using filters through a series of the convolution operation. It extracts the spatial features relevant to the network by observing the non-linear correlation between input-output pairs [18]. Joint 3 Regressor's DCNN takes a 2D input and performs a series of 2D convolutions in several layers to learn the relationship between input and output. Joint Regressor is composed of several layers to first learn the basic features, and as it gets deeper, it learns deeper hidden features that map non-linear relationship between input and output. For the purpose of mapping signals to joint locations, we observe through a series of finetuning processes that 5-layers of stacked convolution with 2 convolution layers in each stack yield the best result than a vanilla DCNN. Stacked representation provides depth to the network so it can learn complex hidden representations [19]. We also apply batch normalization after each stacked layer to ensure normalization and prevent overfitting. The five 2D stacked convolutional layers are connected to a flatten layer that converts the input to a 1D abstract feature of size 512, and then, pass it through two fully connected layers of size 128 and 63, respectively, to finally give output as the 3D location of 21 joints. FIG. 2(b) (Table I) shows the detailed network parameters.

Height Classifier: The objective of the Height Classifier is to assist the Joint Regressor in learning the association between diverse postures of the same person. Since the skeleton of a person typically depends upon her height [20], incorporating height information can make the model generalizable to many individuals with very little or no finetuning. A user could input her ground truth height to the monitoring system, and MiSleep can constrain the output from the Joint Regressor by comparing the predicted height w.r.t. the ground truth, and backpropagating the error to rectify the prediction of joint locations. Instead of predicting the actual height, we employ a classifier by quantizing human heights into discrete values, and then predicting the class labels associated with the quantization. The reason behind designing the model in such a way is two fold. First, it is relatively easier to achieve higher accuracy in predicting a class label than regressing exact height when we operate with small samples from a diverse population. Second, since human heights are limited to a certain deterministic range (e.g., in the US, the average height ranges 163 to 179 cm [21]), it is well-suited to discretize them into range bins, instead of regressing a real value of height, where the network could suffer from out-of-range issues.

To learn the association between height and sleep postures to mmWave signals, Height Classifier takes input from the flatten layer in the Joint Regressor and uses a Multilayer Perceptron (MLP) to output a height classification. MLP is a neural network with one or more hidden layers of neurons that are fully connected in each layer to learn the mapping between input and output. MLP in the Height Classifier comprises three hidden layers with 256, 128, and 64 neurons and an output layer with the number of neurons equal to the number of height classes. We apply ReLU activation in each layer and a Softmax activation in the output layer, which outputs probabilities associated with the labels, and we select the label with the highest predicted probability.

Total Loss Function: We train the Joint Regressor and the Height Classifier jointly by designing a custom loss function to ensure that the network converges to an optimal value. For N number of total joints, the loss for the Joint Regressor is a combination of the Euclidean distance loss, $$L_{ED} = \sqrt{\sum_{i=1}^{N} \left(J_{real}^i - J_{pred}^i\right)^2},$$

between the predicted $$\left(J_{pred}^i\right)$$

and ground truth $$\left(J_{real}^i\right)$$

for $i^{th}$ joint locations and the parent-child distance loss, $$L_{JH} = \sum_{i=1}^{N} \left|PCD_{real}^i - PCD_{pred}^i\right|,$$

that captures the joint hierarchy between predicted $(PCD_{pred}^i)$ and ground truth $(PCD_{real}^i)$ distance of $i^{th}$ joint. The loss function in the Height Classifier is a categorical cross-entropy loss, $$L_{HC} = -\sum_{i=1}^{K} \left(y_i^{real} \cdot \log y_i^{pred}\right),$$

between the $i^{th}$ predicted $$\left(y_i^{pred}\right)$$

and ground truth

8

$$\left(y_i^{real}\right)$$

label of height for K number of class labels, which provides a good quantitative measure in distinguishing probability distributions of discrete categories. The total loss can be expressed as $L_{Total}=\lambda_1 \cdot L_{ED}+\lambda_2 \cdot L_{JH}+\lambda_3 \cdot L_{HC}$, where $\lambda_1$, $\lambda_2$, and $\lambda_3$ are the hyperparameters that govern the contribution of each loss to the entire network.

2.2. Results

Error in Estimating 3D Location of Body Joints: We evaluate the performance of MiSleep's Rest Network in predicting the 3D location of body joints during sleep. For a baseline performance, we first use a small-scale dataset of about 9730 samples collected from three volunteers, (2 females and 1 male, height varying from 155 cm to 178 cm) with the lowest and highest height among all volunteers, performing 5 different sleep postures and their variations, and then evaluate the performance across all 8 volunteers. After synchronizing and resampling, we label the volunteers' height into discrete categories. Then, we randomly select about 8700 samples for training and about 1030 samples for testing. All our samples are evenly distributed across all postures. During training, we use 20% of the training samples for validation. The baseline results include the performance of the Joint Regressor in terms of the Euclidean distance between the ground truth and predicted joint locations.

Figure 4A:
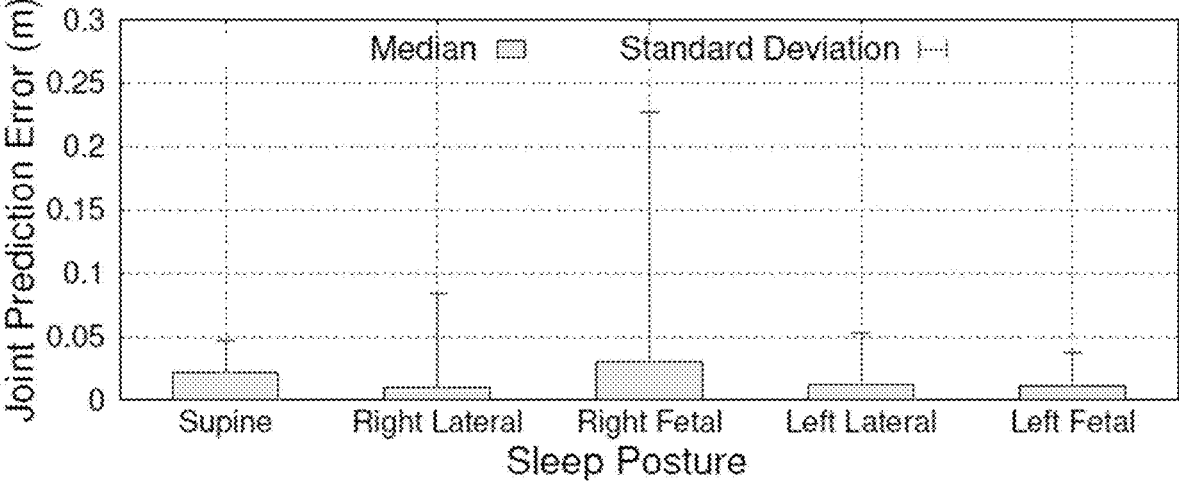
FIG. 4(a) graphically illustrates the performance of the presently disclosed exemplary system (MiSleep), showing plots of the aggregated errors from all joints, separated in terms of their sleep postures.
Figure 5:
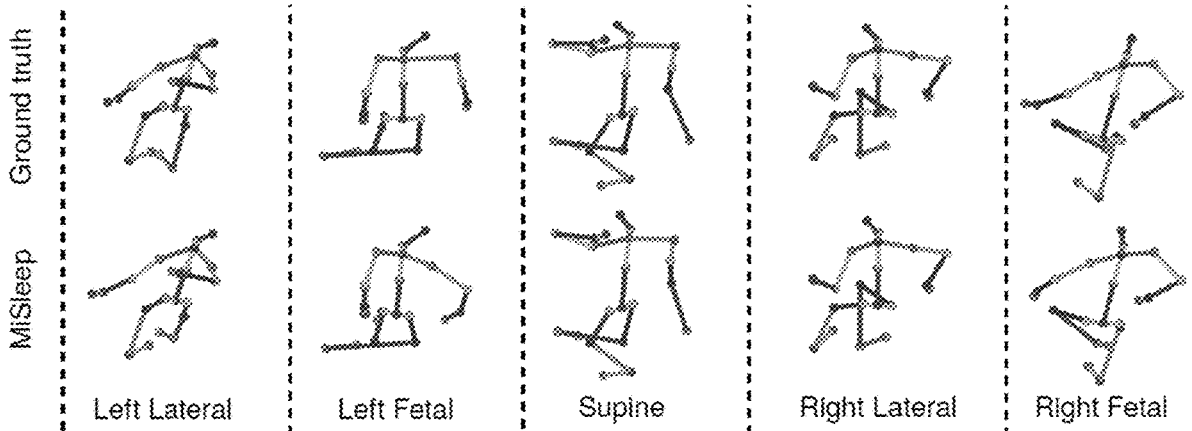
FIG. 5 diagrammatically illustrates top-views of a plurality of skeletons for various exemplary sleep postures predicted by an exemplary embodiment of the presently disclosed MiSleep subject matter.

FIG. 3 graphically illustrates median and standard deviation data for a presently disclosed exemplary system (MiSleep's) prediction errors for 21 joints across 5 poses for 3 volunteers. FIG. 3 further illustrates that for all 21 joints, median error is always less than 4.1 cm. However, one can observe a very high standard deviation across joints 14, 15, 16, 19, and 20 (left knee, left ankle, left foot, right ankle, and right foot). To investigate this issue further, FIG. 4(a) graphically illustrates the performance of the presently disclosed exemplary system (MiSleep), showing plots of the aggregated errors from all joints, separated in terms of their sleep postures. FIG. 4(a) shows that a majority of the errors are from the right fetal, i.e., a curled up posture. The reason for such high error could be due to the inability of the ground truth device to produce accurate joint locations for curled up postures. But the joints that are critical to facilitate a sleep posture monitoring application can be predicted accurately by MiSleep. FIG. 5 shows top-view of skeletons for various sleep postures predicted by MiSleep. These results demonstrate that MiSleep can predict the 3D location of body joints accurately.

Effect of Height Classifier: MiSleep uses the output from the Height Classifier to finetune its Joint Regressor to improve its generalization ability and refine the prediction. To understand the benefit of the Height Classifier, we estimate the absolute 3D joint location errors with and without using it in the model. To this end, we first train the Rest Network without the classifier on about 6500 samples collected from three volunteers, and test it on another set of about 2000 samples. Furthermore, we build the Height Classifier into the network and feed its loss function to finetune the output of the Joint Regressor. Then, we evaluate the performance with the same set of training and testing samples.

Figure 4B:
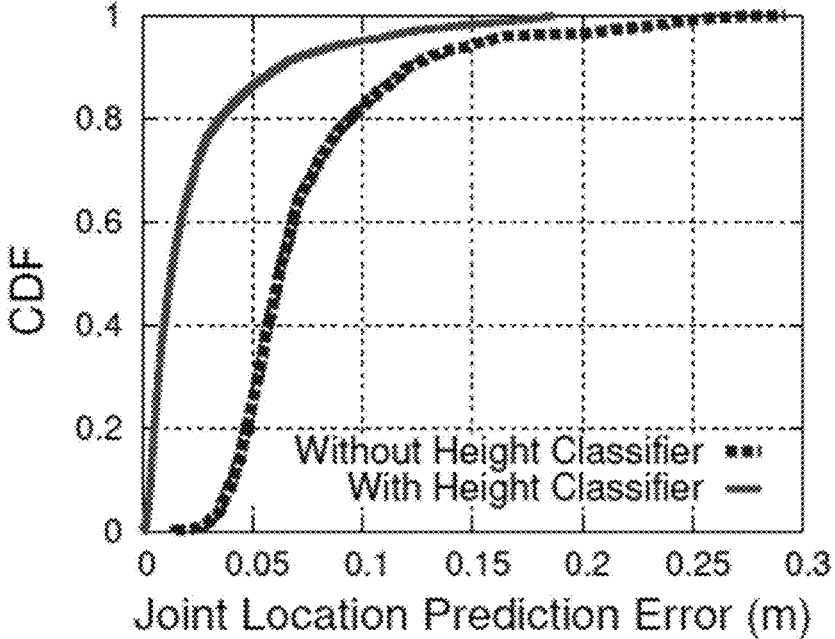
FIG. 4(b) graphically illustrates exemplary performance of the presently disclosed Rest Network with and without presently disclosed Height Classifier features.

FIG. 4(b) graphically illustrates the performance of the Rest Network with and without the Height Classifier. We observe that MiSleep predicts joint locations with median and 90th percentile errors of 6.22 cm and 12.12 cm, respectively, without the Height Classifier. However, by incorporating the classifier, we observe a better prediction with median and 90th percentile errors of 1.3 cm and 6.24 cm, respectively. This is because the network can better associate height information of an individual with variations in sleep postures, which, in turn, enable better joint location estimation from the reflections.

Effect of Number of Volunteers: To evaluate the generalizability of MiSleep's Rest Network for diverse volunteers, we now perform an ablation study. Here, we would like to understand the performance and amount of finetuning required for new, unseen volunteers for MiSleep. To this end, we randomly select 2000 test samples from 8 volunteers, including all 5 sleep postures, with 250 samples from each volunteer. These are unseen data for MiSleep's Rest Network. We then create a training set of about 3000 samples from one volunteer and train MiSleep's Rest Network. We consider it as a base model. We then evaluate the performance on the test samples that include data from all volunteers by calculating absolute joint location error across all 21 joints and the absolute error in height prediction. Then, we progressively add 2 new volunteers' datasets and finetune the base model, and test on the same set of test samples for 8 volunteers.

Figure 6A:
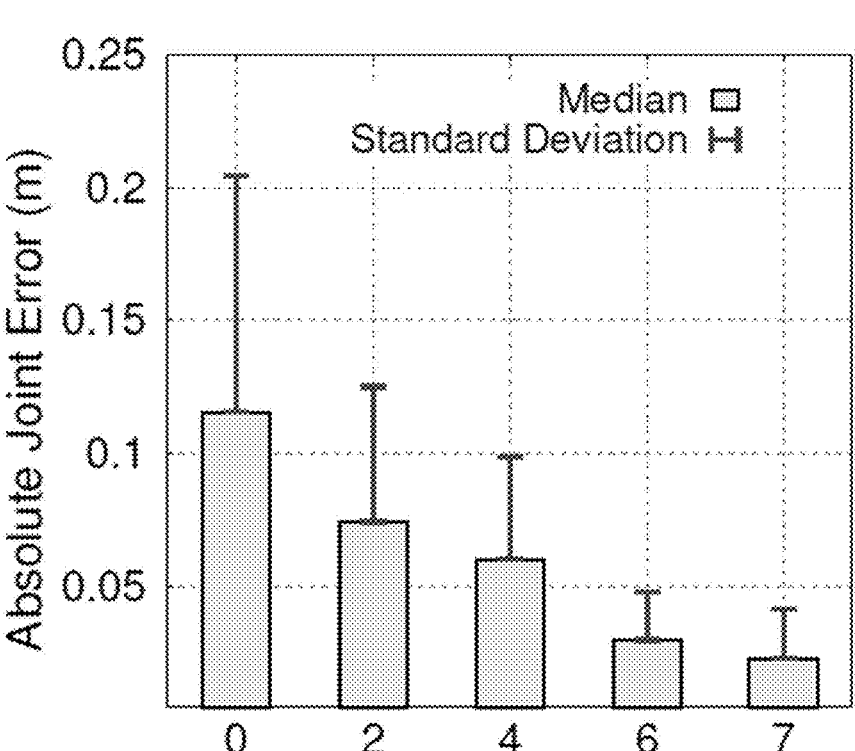
FIG. 6(a) graphically illustrates median and standard deviation data for joint errors of presently disclosed technology versus number of additional volunteers (subjects)
Figure 6B:
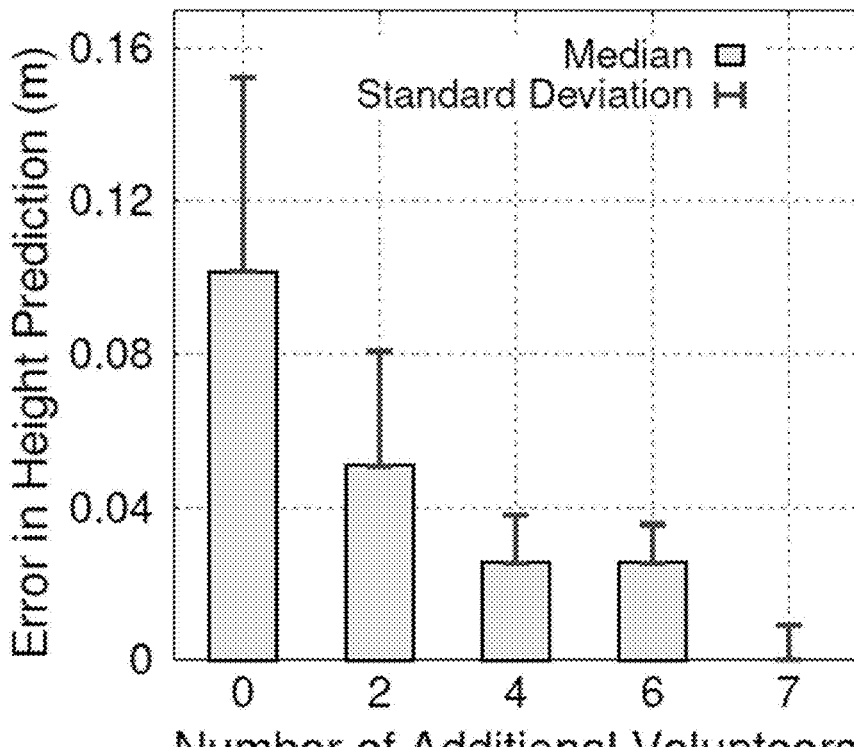
FIG. 6(b) graphically illustrates median and standard deviation data for height errors of presently disclosed technology versus number of additional volunteers (subjects).

FIG. 6(a) graphically illustrates median and standard deviation data for joint errors of presently disclosed technology versus number of additional volunteers (subjects), while FIG. 6(b) graphically illustrates median and standard deviation data for height errors of presently disclosed technology versus number of additional volunteers (subjects). Thus, FIGS. 6(a) and 6(b) graphically represent the exemplary performance of presently disclosed MiSleep technology with different levels of finetuning. The presently disclosed subject matter indicates that MiSleep generalizes across multiple volunteers with only a little finetuning. With zero additional volunteers for the base model, the network is unable to capture variations in sleep posture and its relation to the height of varying individuals. We see that the median joint location error is very high, 11.6 cm, and the predicted body joints may not be usable in practice. Similarly, the median error in the predicted height of the unseen volunteers could be 10.2 cm, which is highly inaccurate. This is intuitive since the network has learned from the dataset of only one volunteer, which results in both body joint and absolute height errors. However, by finetuning the network with 2 additional volunteers' datasets for 500 epochs, we see an improvement in prediction as median errors for joint locations and height decrease to 7.5 cm and 5.08 cm, respectively. This is because presently disclosed MiSleep technology can learn feature associations between individuals and their sleep posture to capture the correlation between mmWave reflections and human body shape. Such improvements are also consistent in both the joint locations and height prediction, as we increase the number of volunteers for finetuning.

In summary, MiSleep predicts 3D location of human body joints during sleep with accuracy on par with the existing vision-based system with only mmWave signals.

This written description uses examples to disclose the presently disclosed subject matter, including the best mode, and also to enable any person skilled in the art to practice the presently disclosed subject matter, including making and using any devices or systems and performing any incorporated methods. The patentable scope of the presently disclosed subject matter is defined by the claims, and may include other examples that occur to those skilled in the art. Such other examples are intended to be within the scope of the claims if they include structural and/or step elements that do not differ from the literal language of the claims, or if they include equivalent structural and/or elements with insubstantial differences from the literal languages of the claims. In any event, while certain embodiments of the disclosed subject matter have been described using specific terms, such description is for illustrative purposes only, and it is to be understood that changes and variations may be made without departing from the spirit or scope of the subject matter. Also, for purposes of the present disclosure, the terms "a" or "an" entity or object refers to one or more of such entity or object. Accordingly, the terms "a", "an", "one or more," and "at least one" can be used interchangeably herein.

REFERENCES

[1] Lisa Matricciani and Yu Sun Bin and Tea Lallukka and Erkki Kronholm and Melissa Wake and Catherine Paquet and Dorothea Dumuid and Tim Olds, "Rethinking the Sleep-Health Link," *Sleep Health*, vol. 4, no. 4, 2018.

[2] Jason J. Liu and Wenyao Xu and Ming-Chun Huang and Nabil Alshurafa and Majid Sarrafzadeh and Nitin Raut and Behrooz Yadegar, "Sleep Posture Analysis Using a Dense Pressure Sensitive Bedsheet," *Pervasive and Mobile Computing*, vol. 10, 2014.

[3] The SUN, "DREAM TEAM People Are Arguing About What is The Best Position to Sleep in but Which One Are You?" 2020. [Online]. Available: https://www.thesun-.co.uk/fabulous/10791045/sleep-position-best-people-ar-gue-night/[4]

[4] Lee, Hedok and Xie, Lulu and Yu, Mei and Kang, Hongyi and Feng, Tian and Deane, Rashid and Logan, Jean and Nedergaard, Maiken and Benveniste, Helene, "The Effect of Body Posture on Brain Glymphatic Transport," *Journal of Neuroscience*, vol. 35, no. 31, 2015.

[5] Tamis Pin and Beverley Eldridge and Mary P Galea, "A Review of the Effects of Sleep Position, Play Position, and Equipment Use on Motor Development in Infants," *Developmental Medicine and Child Neurology*, vol. 49, no. 11, 2007.

[6] Gustavo Desouzart and Rui Matos and Filipe Melo and Ernesto Filgueiras, "Effects of Sleeping Position on Back Pain in Physically Active Seniors: A Controlled Pilot Study," Work, vol. 53, no. 2, 2013.

[7] Simon A. Joosten and Denise M. O'Driscoll and Philip J. Berger and Garun S. Hamilton, "Supine Position Related Obstructive Sleep Apnea in Adults: Pathogenesis and Treatment," *Sleep Medicine Reviews*, vol. 18, no. 1, 2014.

[8] Stefani, Ambra, and Birgit Hgl, "Sleep in Parkinson's disease," *Neuropsychopharmacology*, vol. 45, no. 1, 2020.

[9] Sleep Foundation, "Best Sleeping Positions," 2022. [Online]. Available: https://www.sleepfoundation.org/sleeping-positions

[10] Johns Hopkins, "Choosing the Best Sleep Position," 2022. [Online]. Available: https://www.hopkinsmedicin-e.org/health/wellness-and-prevention/choosing-the-best-sleep-position

[11] Shinjae Kwon and Hojoong Kim and Woon-Hong Yeo, "Recent Advances in Wearable Sensors and Portable Electronics for Sleep Monitoring," *iScience*, vol. 24, no. 5, 2021.

[12] Amazon, "TACTILUS Mattress Pressure Mapping Sensor System Tactile Force Bed Software Body," 2022. [Online]. Available: https://www.amazon.com/TACTILUS-Mattress-Pressure-Mapping-Software/

[13] Lee Jaehoon and Min Hong and Sungyong Ryu, "Sleep Monitoring System Using Kinect Sensor," *International Journal of Distributed Sensor Networks,* 2015.

[14] Liu, Shuangjun and Ostadabbas, Sarah, "A Vision-Based System for In-Bed Posture Tracking," in 2017 *IEEE International Conference on Computer Vision Workshops (ICCVW),* 2017.

[15] Zhang, Feng and Wu, Chenshu and Wang, Beibei and Liu, K. J. Ray, "mmEye: Super-Resolution Millimeter Wave Imaging," *IEEE Internet of Things Journal,* vol. 8, no. 8, 2021.

[16] Chen, Tianlang and Fang, Chen and Shen, Xiaohui and Zhu, Yiheng and Chen, Zhili and Luo, Jiebo, "Anatomy-aware 3D Human Pose Estimation with Bone-based Pose Decomposition," 2020. [Online]. Available: https://arxiv.org/abs/2002.10322

[17] Blazevic, Martin and Brkic, Karla and Hrkac, Tomislav, "Towards Reversible De-Identification in Video Sequences Using 3D Avatars and Steganography," 2015. [Online]. Available: https://arxiv.org/abs/1510.04861

[18] Albawi, Saad and Mohammed, Tareq Abed and Al-Zawi, Saad, "Understanding of a convolutional neural network," in 2017 *International Conference on Engineering and Technology (ICET),* 2017.

[19] Karen Simonyan and Andrew Zisserman, "Very Deep Convolutional Networks for Large-Scale Image Recognition," 2015. [Online]. Available: https://arxiv.org/abs/1409.1556

[20] Porter, A., "The Prediction of Physique from the Skeleton." *International Journal of Osteoarchaeol,* vol. 9, 1999.

[21] World Population Review, "Average Height by State 2022," 2022. [Online]. Available: https://worldpopulationreview.com/state-rankings/average-height-by-state

What is claimed is:

1. Method for automatically classifying sleep postures of a human subject from millimeter-wave (mmWave) wireless signals reflecting from the human subject, comprising:

training a Deep Convolutional Neural Network (DCNN) learning model, based on inputs of ground truth sleep postures of a plurality of human subjects and generated input and output pairs of mmWave reflected signals from the plurality of human subjects and respectively corresponding with the ground truth inputs, to learn the association between millimeter-wave (mmWave) wireless signals reflected from a human subject and joint locations of a human subject;

operating the trained DCNN learning model to process further input data thereto, to determine and output identification of diverse sleep postures during the rest state of the human subject;

transmitting millimeter-wave (mmWave) wireless signals configured for interacting with a human subject;

receiving millimeter-wave (mmWave) wireless signals reflecting from the human subject;

operating the DCNN based on the received signal reflections for directly predicting joint locations of the human subject; and operating the DCNN for classifying the sleep posture of the human subject into one of a plurality of diverse sleep postures during the rest state of the human subject, based on predicted joint locations of the human subject.

2. Methodology according to claim 1, wherein predicting comprises predicting the 3D locations of a plurality of key body joints based on the received signal reflections, and based on evaluating a hierarchal relationship of arrangements for the body joints of a given human subject.

3. Method according to claim 1, further comprising:

using at least one existing 5G wireless device in a home setting for transmitting millimeter-wave (mmWave) wireless signals to the human subject, to provide a single-person sleep posture monitoring system with mmWave-based posture monitoring under no light without being privacy-invasive.

4. Method according to claim 1, further comprising refining the training of the DCNN for a specific human subject user based on the ground truth height of the specific human subject user.

5. Method according to claim 1, further comprising monitoring a human subject using an observation arrangement in which a human subject is reclined on a bed, and at least one mmWave transmitter and receiving antenna is positioned in a range from 2 to 5 meters away from the human subject, with the antenna having a beamwidth which covers the whole bed area of the bed on which the human subject is reclined.

6. Method according to claim 1, wherein the DCNN comprises an architecture of a plurality of stacked neural networks having at least two convolution layers each, all using ReLU activation in each layer, followed by a flatten layer.

7. Method according to claim 6, wherein the DCNN comprises further architecture of a pair of paths in parallel based on the output of the flatten layer, with one path comprising a joint regressor to output 3D joint locations and the other path comprising a height classifier to output height labels.

8. One or more tangible, non-transitory computer-readable media that collectively store instructions that, when executed, cause a computing device including one or more processors to perform operations, the operations comprising automatically identifying diverse sleep postures during the rest state of a human subject from millimeter-wave (mmWave) wireless signals reflecting from the human subject, by:

training a Deep Convolutional Neural Network (DCNN) learning model, based on inputs of ground truth sleep postures of a plurality of human subjects and generated input and output pairs of mmWave reflected signals from the plurality of human subjects and respectively corresponding with the ground truth inputs, to learn the association between millimeter-wave (mmWave) wireless signals reflected from a human subject and joint locations of a human subject;

operating the trained DCNN learning model to process further input data thereto, to determine and output identification of diverse sleep postures during the rest state of the human subject;

transmitting millimeter-wave (mmWave) wireless signals configured for interacting with a human subject;

receiving millimeter-wave (mmWave) wireless signals reflecting from the human subject;

operating the DCNN based on the received signal reflections for directly predicting joint locations of the human subject; and operating the DCNN for classifying the sleep posture of the human subject into one of a plurality of diverse sleep postures during the rest state of the human subject, based on predicted joint locations of the human subject.

9. The one or more tangible, non-transitory computer-readable media according to claim 8, wherein predicting comprises predicting the 3D locations of a plurality of key body joints based on the received signal reflections, and based on evaluating a hierarchal relationship of arrangements for the body joints of a given human subject.

10. The one or more tangible, non-transitory computer-readable media according to claim 8, further comprising operations of:

using at least one existing 5G wireless device in a home setting for transmitting millimeter-wave (mmWave) wireless signals to the human subject, to provide a single-person sleep posture monitoring system with mmWave-based posture monitoring under no light without being privacy-invasive.

11. The one or more tangible, non-transitory computer-readable media according to claim 8, further comprising operations of refining the training of the DCNN for a specific human subject user based on the ground truth height of the specific human subject user.

12. The one or more tangible, non-transitory computer-readable media according to claim 8, further comprising operations of monitoring a human subject using an observation arrangement in which a human subject is reclined on a bed, and at least one mmWave transmitter and receiving antenna is positioned in a range from 2 to 5 meters away from the human subject, with the antenna having a beamwidth which covers the whole bed area of the bed on which the human subject is reclined.

13. The one or more tangible, non-transitory computer-readable media according to claim 8, wherein the DCNN comprises an architecture of a plurality of stacked neural networks having at least two convolution layers each, all using ReLU activation in each layer, followed by a flatten layer.

14. The one or more tangible, non-transitory computer-readable media according to claim 13, wherein the DCNN comprises further architecture of a pair of paths in parallel based on the output of the flatten layer, with one path comprising a joint regressor to output 3D joint locations and the other path comprising a height classifier to output height labels.

* * * * *